United States Patent
Rouh et al.

(10) Patent No.: US 10,142,606 B2
(45) Date of Patent: Nov. 27, 2018

(54) DEVICE FOR USE IN IDENTIFYING OR AUTHENTICATING A SUBJECT

(71) Applicant: MORPHO, Issy les Moulineaux (FR)

(72) Inventors: Alain Rouh, Vincennes (FR); Benoit Malrat, Pontoise (FR)

(73) Assignee: MORPHO, Issy les Moulineaux (FR)

( * ) Notice: Subject to any disclaimer, the term of this patent is extended or adjusted under 35 U.S.C. 154(b) by 378 days.

(21) Appl. No.: 14/863,785

(22) Filed: Sep. 24, 2015

(65) Prior Publication Data
US 2016/0094833 A1  Mar. 31, 2016

(30) Foreign Application Priority Data

Sep. 26, 2014 (FR) ..................... 14 59133

(51) Int. Cl.
*H04N 13/02* (2006.01)
*A61B 5/00* (2006.01)
*A61B 5/117* (2016.01)
*G06K 9/00* (2006.01)
*G06K 9/20* (2006.01)
(Continued)

(52) U.S. Cl.
CPC ....... *H04N 13/0242* (2013.01); *A61B 5/0062* (2013.01); *A61B 5/0077* (2013.01); *A61B 5/117* (2013.01); *G06K 9/00006* (2013.01); *G06K 9/00255* (2013.01); *G06K 9/00288* (2013.01); *G06K 9/00604* (2013.01); *G06K 9/00617* (2013.01); *G06K 9/209* (2013.01); *G06K 9/00892* (2013.01); *H04N 5/00* (2013.01); *H04N 7/186* (2013.01); *H04N 2213/001* (2013.01)

(58) Field of Classification Search
CPC ........... H04N 5/00; H04N 7/18; H04N 13/00; G06K 9/00; A61B 5/00
See application file for complete search history.

(56) References Cited

U.S. PATENT DOCUMENTS

2009/0041309 A1* 2/2009 Kim .................. G06K 9/00604
                                                                         382/117
2010/0253816 A1* 10/2010 Hanna .................. G06K 9/209
                                                                         348/262

(Continued)

OTHER PUBLICATIONS

French Preliminary Search Report issued May 19, 2015 in French Application 14 59133, filed on Sep. 26, 2014 (with English Translation of Categories of Cited Documents).

(Continued)

*Primary Examiner* — Maryam A Nasri
(74) *Attorney, Agent, or Firm* — Oblon, McClelland, Maier & Neustadt, L.L.P.

(57) ABSTRACT

A device for use in identifying or authenticating a subject positioned in an acquisition volume on the basis of at least one biometric characteristic of the subject, the device including in succession, in offset manner along a camera placement axis: a first camera; a second camera; and a third camera; the optical axes of the first and second cameras forming between them an angle strictly less than 10°, and the optical axis of the third camera intersecting the optical axes of the first and second cameras, the optical axes of the first and second cameras each forming an angle less than or equal to 5° relative to a normal axis perpendicular to the camera placement axis.

9 Claims, 6 Drawing Sheets

(51) Int. Cl.
*H04N 5/00* (2011.01)
*H04N 7/18* (2006.01)

(56) References Cited

U.S. PATENT DOCUMENTS

2012/0219279 A1 8/2012 Hanna et al.
2014/0140685 A1 5/2014 Hanna et al.

OTHER PUBLICATIONS

Shihong Lao, et al., "3D Template Matching for Pose Invariant Face Recognition Using 3D Facial Model Built with Isoluminance Line Based Stereo Vision", Proceedings of the International Conference on Pattern Recognition (ICPR), IEEE Computer Soc., vol. 2, 2000, 6 pgs.

\* cited by examiner

DEVICE FOR USE IN IDENTIFYING OR AUTHENTICATING A SUBJECT

BACKGROUND OF THE INVENTION

The invention relates to devices suitable for identifying or authenticating a subject, and to methods making use of such devices.

Face recognition devices are known that include a plurality of cameras in order to cover an acquisition volume as is needed for matching morphologies and for ergonomic comfort, the cameras being arranged so as to cover as large as possible a field with the fields of the cameras overlapping sufficiently. In such devices, the optical axes of the cameras may be parallel and horizontal as in the SmartGate® system. By way of example, those systems make it possible to authenticate a subject by confirming or invalidating the alleged identity of a subject on the basis of one or more images of the subject taken by the cameras and after comparing them with reference data stored in a data storage medium.

Other systems may use cameras having optical axes that coincide in order to maximize the volume in which the subject comes within the field of the various cameras. Such systems enable triangulation to be performed and thus make it possible to perform three-dimensional (3D) reconstruction of the position of a zone of the subject's face by using cameras having fields of view that overlap.

Nevertheless, both of the two above-described types of system can be less than optimal for constituting a multi-biometric system for two-dimensional (2D) face recognition and for iris recognition relying on 3D locating of the eyes by triangulation.

Furthermore, systems having optical axes that coincide have at least one camera with its optical axis pointing upwards. This can lead to the camera being dazzled by sunlight or by lighting situated high up, and can thus lead to a reduction in identification performance.

Furthermore, it can be desirable to minimize the size of devices for identifying or authenticating a subject, in particular when such devices are for use in airport zones.

There thus exists a need for obtaining devices that are useful for identifying or authenticating a subject and that are suitable for being used in satisfactory manner both for performing face recognition of the subject and for determining the 3D position of a zone of the subject's face.

There also exists a need for obtaining devices that are useful for identifying or authenticating a subject and that present performance that is little affected by ambient lighting conditions.

There also exists a need for obtaining devices that are useful for identifying or authenticating a subject and that are of limited size.

There also exists a need for obtaining devices that are useful for identifying or authenticating a subject and that present calculation times and operating costs that are small.

OBJECT AND SUMMARY OF THE INVENTION

For this purpose, in a first aspect, the invention provides a device for use in identifying or authenticating a subject positioned in an acquisition volume on the basis of at least one biometric characteristic of the subject, the device comprising in succession, in offset manner along a camera placement axis: a first camera; a second camera; and a third camera; the optical axes of the first and second cameras forming between them an angle strictly less than 10°, and the optical axis of the third camera intersecting the optical axes of the first and second cameras.

In a subject identification method, the device may receive images of an unknown subject, and after comparing that data with reference data stored in a data storage medium, it may determine the identity of that subject. In a subject authentication method, the device confirms or invalidates the alleged identity of a subject on the basis of one or more images of the subject and after making a comparison with reference data stored in a data storage medium. Identification or authentication may be performed in automatic manner. The data storage medium storing the reference data may be incorporated in the device. In a variant, the data storage medium may be present in a computer system external to the device, the device then being configured to exchange data with said computer system.

A biometric characteristic of a subject is a biological characteristic of the subject that is useful for identification purposes. As biometric characteristics that are suitable, mention may be made of characteristics relating to the subject's fingerprints, to the subject's irises, or indeed to the shape of the subject's face.

The term "the optical axis of the third camera intersecting the optical axes of the first and second cameras" should be understood to mean that the optical axis of the third camera is not parallel to the optical axes of the first and second cameras, the optical axis of the third camera being directed towards the optical axes of the first and second cameras in order to intersect them.

The device of the invention presents two functions. Firstly, it can be used for performing 2D face recognition using some or all of the images from the first, second, and third cameras. Secondly, it makes it possible to determine the position of a zone of the subject's face by triangulation using at least two of the first, second, and third cameras. In particular, it is possible to determine the position of a zone of the subject's face by triangulation using the third camera and at least one of the first and second cameras. In a variant, it is possible to determine the position of a zone of the subject's face by triangulation using only the first and second cameras.

Thus, the device of the invention has a plurality of cameras in a particular arrangement that is suitable for performing in satisfactory manner both face recognition from 2D images of a subject and for stereoscopically determining the position of at least one zone of the subject's face, e.g. the positions of the eyes. As described in greater detail below, an iris image taking system or a 3D face recognition system may be guided on the basis of the 3D position of a zone of the subject's face as determined by triangulation.

In a first embodiment, the optical axes of the first and second cameras may form between them an angle that is less than or equal to 5°, or indeed they may be substantially parallel to each other, or they may be exactly parallel (angle of 0°).

Preferably, the optical axes of the first and second cameras may each form an angle less than or equal to 10°, e.g. less than or equal to 5°, relative to a normal axis perpendicular to the camera placement axis. In an embodiment, the optical axes of the first and second cameras may both be parallel to the normal axis.

Such configurations are advantageous since they serve to minimize the angle formed between the normal to the subject's face and the optical axes of the first and second cameras so as to obtain very good performance in 2D face recognition.

In an embodiment, the optical axes of the first, second, and third cameras need not coincide (i.e. they need not intersect at a single point).

In an embodiment, the camera placement axis may be substantially vertical. Such a configuration makes it possible advantageously to further improve the performance and the ergonomics of the device. Thus, the device may be such that:

the first camera is placed at a first height;
the second camera is placed at a second height higher than the first height; and
the third camera is placed at a third height higher than the second height.

Unless specified to the contrary, the heights of elements of the device (cameras, iris image taking systems, . . . ) are measured perpendicularly relative to the surface for positioning the subject in the acquisition volume. The positioning surface corresponds to the surface on which the subject is to be present during identification or authentication. Thus, the height of this surface is taken as a reference height (equal to 0).

In an embodiment, the optical axis of the third camera and at least one of the optical axes of the first and second cameras extend towards a positioning surface on which the subject is to be present in order to perform identification or authentication. In particular, under such circumstances, one of the optical axes of the first and second cameras may be parallel to the normal axis. In a variant, each of the optical axes of the first and second cameras may extend towards a positioning surface on which the subject is to be present in order to perform identification or authentication.

In a variant, the optical axis of the third camera may extend towards a positioning surface on which the subject is to be present in order to perform identification or authentication, and the optical axes of the first and second cameras may both be parallel to the normal axis.

Configurations in which the optical axes of the cameras are either parallel to the normal axis (i.e. horizontal when the camera placement axis extends vertically), or else extend towards the positioning surface (i.e. downwards relative to the camera placement axis) are such that none of the optical axes of the cameras is directed upwards (i.e. towards heights of increasing value along the camera placement axis).

These configurations make it possible advantageously to give the device very good robustness against lighting conditions, since not having a camera with its optical axis pointing upwards avoid having a camera that might be dazzled by sunlight or by artificial light sources situated high up.

Preferably, the superposition of the fields of the first and second cameras may cover the entire acquisition volume, and the following conditions may be satisfied:

the angle $\alpha_{23}$ formed between the optical axis of the third camera and a normal axis perpendicular to the placement axis of the cameras is such that:

$$(\arctan(h'_{23}/d)-\beta_{23}/2) \leq \alpha_{23} \leq 1.1 \times (\arctan(h'_{23}/d)-\beta_{23}/2);$$

and the field angle $\beta_{23}$, along the height of the third camera satisfies the following condition:

$$\beta_{23} \geq 2 \times (\alpha_{23} + \arctan((h_v - h'_{23})/d));$$

where $h'_{23}$ designates the height of the third camera measured relative to the height of the bottom boundary of the acquisition volume, $h_v$ designates the height of the acquisition volume, and d designates the distance measured along the normal axis between the third camera and the acquisition volume.

The term "superposition of the fields of the first and second cameras" is used to mean the union (i.e. addition) of those fields. The above mathematical condition imposed on $\beta_{23}$, in combination with the above mathematical condition imposed on $\alpha_{23}$ implies in particular that the field of the third camera needs to be sufficient to cover both the top portion and the bottom portion of the acquisition volume.

Such values for the angle of inclination of the optical axis of the third camera correspond to an optimum situation in which the angle of inclination is sufficient to enable triangulation to be performed with at least one of the first and second cameras throughout the acquisition volume, this angle of inclination also being small enough to avoid having too great an angle relative to the direction of the normal to the faces of the tallest subjects. In addition, the optical axis of a third camera presenting such angles of inclination advantageously forms a small angle relative to the normal to the faces of the shortest subjects, whose faces will be facing upwards in order to read a screen situated on the device, for example. Such angles of inclination for the optical axis of the third camera also make it possible to limit any risk of this camera being dazzled by sunlight or by light sources situated high up such as ceiling lights.

Thus, such angles of inclination for the optical axis of the third camera make it possible firstly to obtain good performance in terms of triangulation when using the third camera, because the entire acquisition volume is covered by the field of the third camera. Secondly, such an angle of inclination for the optical axis of the third camera remains relatively limited, which is advantageous when the third camera performs not only the function of a stereoscopic camera, but also the function of a 2D camera for face recognition.

Preferably, $\alpha_{23}$ may be equal to $(\arctan(h'_{23}/d)-\beta_{23}/2)$.

In an embodiment, in addition to the first, second, and third cameras, the device may include an incorporated iris image taking system. This system is a system for taking images of the texture of at least one iris and, by way of example, it is in communication with an iris recognition system. Said iris recognition system is configured to recognize the iris of at least one of the subject's eyes on the basis of at least one image of one or both of the irises of the subject's eyes as taken by the iris image taking system. The iris image taking system may thus be configured to transmit data to an iris recognition system.

The iris recognition system may be incorporated in the device. In a variant, the iris recognition system is situated outside the device. The iris recognition system includes an image analysis system. On the basis of at least one image of one or both irises of the subject's eyes taken by the iris image taking system, the image analysis system may make it possible to obtain data that is associated with the texture of one or both of the irises of the subject's eyes, this data being useful for recognizing at least one of the irises of the subject's eyes.

In an embodiment, the following three conditions may be satisfied:

the first height lies in the range 130 centimeters (cm) to 150 cm;
the second height lies in the range 150 cm to 170 cm; and
the third height lies in the range 180 cm to 200 cm.

The present invention also provides an automatic door fitted with a device as described above. The present invention also provides an airlock fitted with a device as described above.

The present invention also provides a method of identifying or authenticating a subject that makes use of a device, an automatic door, or an airlock as described above, the method comprising the following steps:

a) positioning the subject in the acquisition volume; and b) performing 2D face recognition of the subject from one or more images of the subject taken by at least one of the first, second, and third cameras.

This 2D face recognition may be performed by the device, or in a variant it may be performed by a computer system external to the device on the basis of data associated with at least one image of the subject taken by at least one of the cameras of the device.

In an implementation, a step c) for determining the position of at least one zone of the face of the subject may be performed by triangulation using at least two of the first, second, and third cameras. In particular, step c) may be performed by triangulation using the third camera and at least one of the first and second cameras. Step c) may be performed after step b). In a variant, step c) is performed before step b). Before step c), a step is performed of detecting at least one zone of the subject's face, e.g. the eyes.

The zone of the face of position that is determined during step c) may be the mouth zone, the nose zone, or indeed the entire face. In an implementation, the positions of the subject's eyes may be determined by triangulation during step c).

In an implementation, a step d) of recognizing at least one iris of the eyes may be performed after step c), step d) comprising the following steps:

d1) acquiring at least one image of at least one of the irises of the eyes of the subject by means of the iris image taking system, the iris image taking system being guided at least by data associated with the positions of the eyes of the subject as determined during step c); and d2) recognizing at least one iris of the eyes of the subject by comparing data associated with said at least one image of one or both irises obtained during step d1) with reference iris data.

The iris image taking system may be guided under electromechanical control. The iris image taking system may also be guided so as to select a sharp image from a video stream obtained on the basis of an estimate of the distance to the subject. It is also possible to use these two aspects in combination: using guidance under electromechanical control for image framing, and using image selection for sharpness.

Such iris recognition may be performed by the device, or in a variant it may be performed by a computer system external to the device.

In a variant or in combination, a step e) of estimating a 3D model of the subject's face may be performed after step c) on the basis of the position of at least one zone of the face as obtained during step c).

In an implementation, the 3D model of the face estimated during step e) may make it possible to perform 3D face recognition of the subject. It is thus possible to use a method in which both 2D face recognition of the subject and 3D face recognition of the same subject are performed. Such 3D face recognition may be performed by the device, or in a variant it may be performed by a computer system external to the device.

One way of performing 3D face recognition on the basis of the 3D position of a zone of the face is described by way of example in the second paragraph on page 641 of the publication by I. A. Kakadiaris, G. Passalis, G. Toderici, N. Murtuza, N. Karampatziakis, and T. Theoharis (2007): "3D face recognition in the presence of facial expressions: an annotated deformable model approach", IEEE Transactions on Pattern Analysis and Machine Intelligence (PAMI) 13 (12).

The estimate made during step e) may also be used for determining images that are good for 2D face recognition. Thus, by way of example, it is possible, after step e), to make a selection from among the images taken by the cameras of the device for the purpose of performing 2D face recognition, this selection being made on the basis of data associated with the estimate made during step e), 2D face recognition then being performed on the basis of the selected images. The estimate made during step e) can also serve to control the cameras of the device in order to acquire images that are good for 2D face recognition.

BRIEF DESCRIPTION OF THE DRAWINGS

Other characteristics and advantages of the invention appear from the following description given with reference to the accompanying drawings, in which.

DETAILED DESCRIPTION OF EMBODIMENTS

Figure 1:
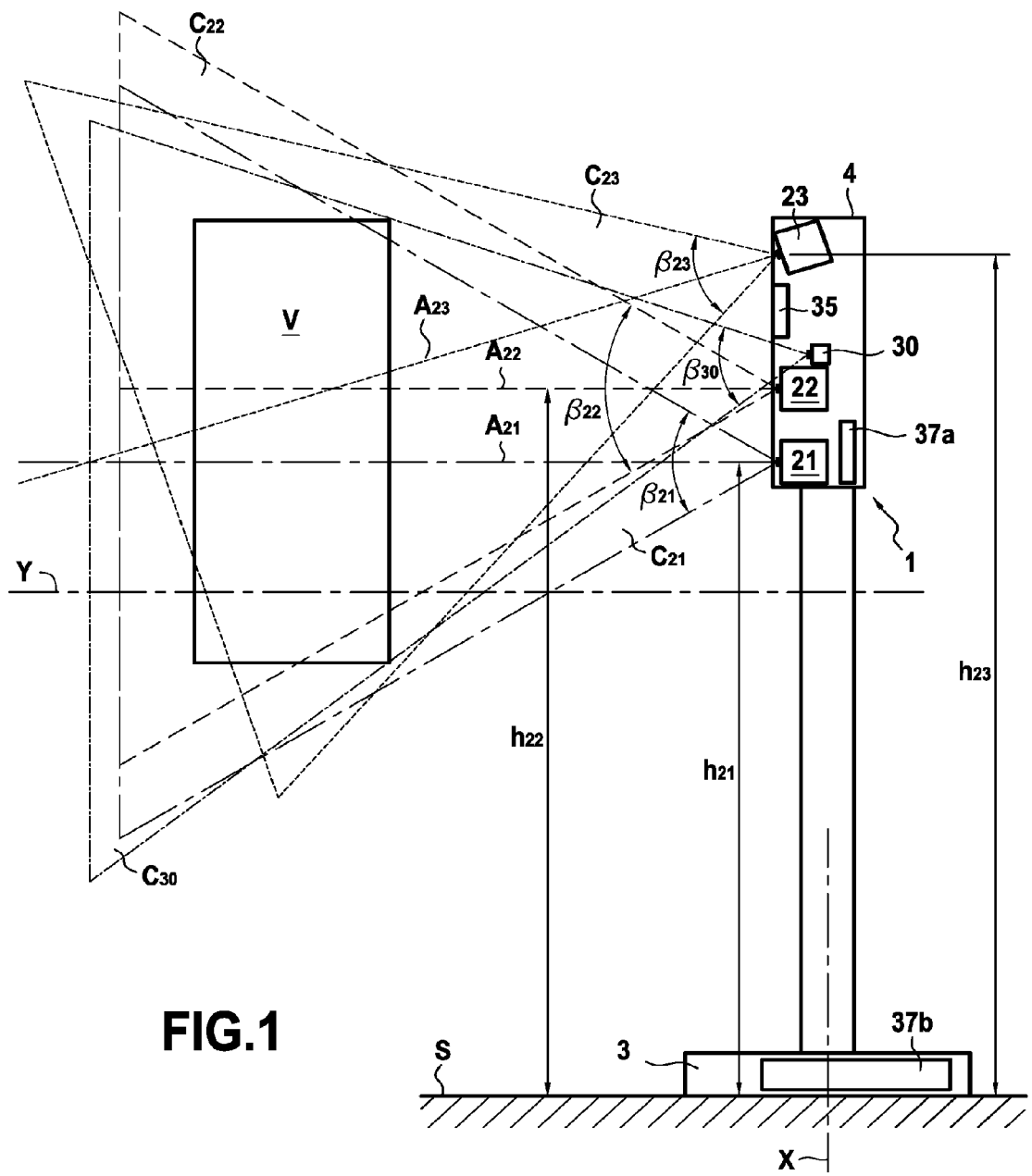
FIG. 1 is a fragmentary longitudinal section of an embodiment of a device of the invention.

FIG. 1 shows a device 1 of the invention. In the example shown, the device 1 is in the form of a stationary device presenting a stand 3 in its bottom portion for providing it with stability on a support surface S on which it is located. As shown, the device 1 may be in the form of a tower. The device 1 of the invention has first, second, and third cameras 21, 22, and 23. The cameras are housed in a frame 4 in order to protect them. The device 1 may advantageously be fitted to an automatic door, for example in an airport. It would not go beyond the ambit of the invention for the device to be of a different shape. In a variant that is not shown, the device does not have a stand and it is fastened to a wall at a height suitable for performing identification or authentication.

As shown in FIG. 1, the first, second, and third cameras are offset in height along a camera placement axis X that corresponds in this example to the long axis of the device 1. In the example shown, the camera placement axis X is vertical when the device 1 is in an operating configuration. More precisely, the first camera 21 is placed nearest to the stand 3 of the device 1 at a first height $h_{21}$, the camera 22 is placed at a second height $h_{22}$ higher than the first height $h_{21}$, and the third camera 23 is placed at a third height $h_{23}$ higher than the second height $h_{22}$. In an embodiment, the cameras 21, 22, and 23 may be in vertical alignment. In a variant, the cameras 21, 22, and 23 are offset in height along the camera placement axis X and they are also offset in width.

The presence of the second camera 22 between the first and third cameras 21 and 23 serves advantageously to improve performance for taller people for whom algorithms for detecting face zones do not give results that are as good when using the first camera. In addition, by increasing the number of cameras involved, using this second camera makes it possible to limit the effects of perspective projection for the camera at the height that best matches the size of the subject, as happens with the SmartGate® system, for example.

Unless mentioned to the contrary, the height of a camera of the device 1 corresponds to the height at which the lens of said camera is located. By way of example, the following first, second, and third heights may be used with the device of the invention: $h_{21}$=140 cm; $h_{22}$=160 cm; and $h_{23}$=190 cm.

More generally, the device 1 may be such that the following three conditions are true when the device is in an operating configuration:

$h_{21}$ lies in the range 130 cm to 150 cm, $h_{21}$ being equal to 140 cm, for example;

$h_{22}$ lies in the range 150 cm to 170 cm, $h_{22}$ being equal to 160 cm, for example; and $h_{23}$ lies in the range 180 cm to 200 cm, $h_{23}$ being equal to 190 cm, for example.

When the device 1 of the invention is fitted to an airport door, such values for $h_{21}$ may be advantageous in avoiding masking due to existing elements in the airport, since lower positions would run the risk of leading to masking. Such values for $h_{21}$ also make it possible to obtain spacing from the third camera that is sufficient to obtain good triangulation accuracy when the third camera is used for triangulation, and such values are also useful for optimizing the performance of 2D analysis algorithms for shorter people if they are not looking upwards.

Such values for $h_{23}$ correspond advantageously to the third camera 23 being placed at a height that is relatively low, thereby enabling the overall size of the device to be limited while still enabling good performance to be obtained in terms of triangulation when the third camera 23 is used for this purpose.

As shown in FIG. 1, the optical axis $A_{21}$ of the first camera 21 may be parallel to the optical axis $A_{22}$ of the second camera 22, and the optical axis $A_{23}$ of the third camera 23 is not parallel to the optical axes $A_{21}$ and $A_{22}$, and it is directed towards those axes. Thus, the optical axis $A_{23}$ intersects the optical axes $A_{21}$ and $A_{22}$. In the example shown, the optical axes $A_{22}$ and $A_{23}$ cross inside the acquisition volume V and the optical axes $A_{21}$ and $A_{23}$ cross outside the acquisition volume V on its side remote from the device 1. Thus, in the example shown, the optical axes $A_{21}$, $A_{22}$, and $A_{23}$ do not coincide (i.e. all three of them do not intersect one another at the same point).

Figure 2:
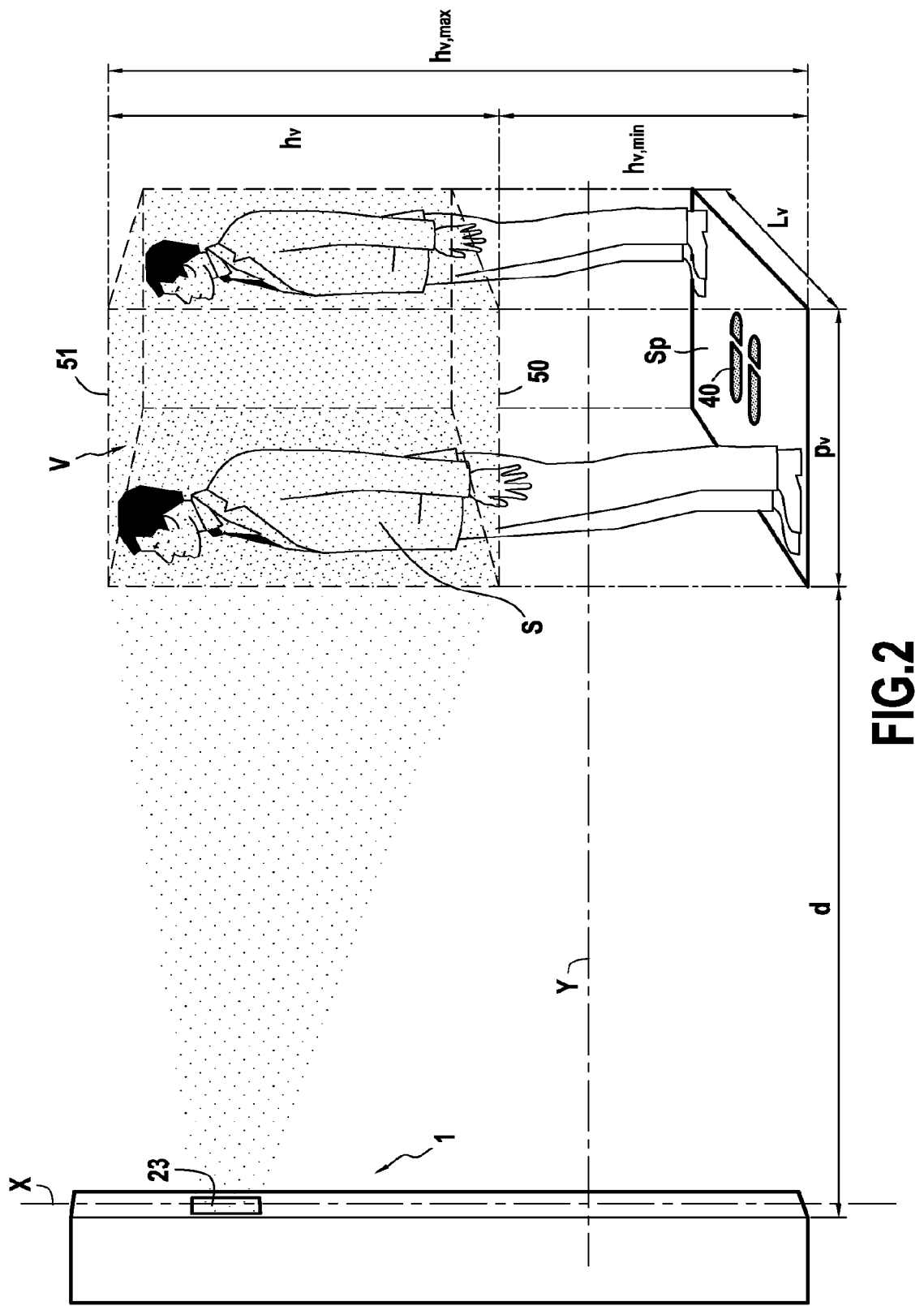
FIG. 2 shows a device of the invention together with its acquisition volume in side view.

In the example shown in FIG. 1, the optical axes $A_{21}$ and $A_{22}$ are parallel to the normal axis Y that is perpendicular to the camera placement axis X. The normal axis Y in the example shown is horizontal. In the example shown, the optical axis $A_{23}$ is at an angle of about 15° to the normal axis Y. More generally, the optical axis $A_{23}$ of the third camera may be at an angle of less than 20° to the normal axis Y. As shown in FIG. 2, the normal axis Y is parallel to the positioning surface $S_p$ of the subject S in the acquisition volume V and it extends between the device 1 and the acquisition volume V. In a variant, it is possible for the optical axes of the first and second cameras to be at a non-zero angle to the normal axis, e.g. an angle that is less than or equal to 10°, or indeed less than or equal to 5°.

In the example shown in FIG. 1, the optical axes $A_{21}$ and $A_{22}$ are horizontal, and the optical axis $A_{23}$ extends towards the positioning surface $S_p$. Such a configuration advantageously serves to limit as much as possible the extent to which the cameras 21, 22, and 23 are dazzled by sunlight or by artificial light sources situated high up. Thus, such a configuration can improve the identification and authentication performance obtained for subjects who are short by limiting the angle between the optical axis $A_{21}$ and the normal to the faces of such subjects.

The fields of the cameras 21, 22, and 23 are respectively referenced $C_{21}$, $C_{22}$, and $C_{23}$ and they are shown in FIG. 1. These fields $C_{21}$, $C_{22}$, and $C_{23}$ are shown in section in FIG. 1. In the example shown in FIG. 1, the field angles in the vertical direction of the cameras 21, 22, and 23 are respectively referenced $\beta_{21}$, $\beta_{22}$, and $\beta_{23}$, and they are substantially equal, e.g. being equal to about 60°. It would not go beyond the ambit of the invention for at least two of the field angles of the cameras in the vertical direction to be different. The entire acquisition volume V is covered by the superposition of the fields of the first and second cameras $C_{21}$ and $C_{22}$. In other words, the acquisition volume is covered over its entire height, over its entire width, and over its entire depth by the superposition of the fields of the first and second cameras. "Adding" the fields $C_{21}$ and $C_{22}$ makes it possible to cover the entire acquisition volume.

The angle of inclination of the optical axis $A_{23}$ may advantageously be selected so as to obtain maximum coverage of the acquisition volume V by the field $C_{23}$. Such a configuration makes it possible advantageously to use the third camera 23 and at least one of the first and second cameras 21 and 22 to perform triangulation in a zone of maximum volume within the acquisition volume V. In particular, the entire acquisition volume V may be covered by the field $C_{23}$ of the third camera 23. Under such circumstances, the field angle of the third camera in the width direction should be sufficient to cover the entire width $L_V$ of the acquisition volume V. In addition, it is advantageous to be in a configuration in which the angle of inclination of the optical axis $A_{23}$ is minimized while still making it possible to cover the entire acquisition volume V by means of the field $C_{23}$ of the third camera 23. Such a configuration makes it possible: i) to perform triangulation throughout the acquisition volume V; and ii) to obtain very good performance for facial recognition of subjects who are tall, the optical axis $A_{23}$ then forming a limited angle relative to the normal to the faces of such subjects.

The device 1 also includes a data storage medium storing information associated with at least one biometric characteristic of at least one subject, or suitable for storing such information. The device 1 is fitted with processor means making it possible to take the video streams from the cameras 21, 22, and 23 and to recognize the face of a subject and to determine the position of at least one zone of the subject's face by triangulation. The device 1 thus has a computer processor system 37a and 37b including in particular a computer configured to process the data obtained while the device 1 is in operation.

In a variant that is not shown, the data storage medium may be present in an computer system external to the device, the device then being configured to exchange data with said computer system. In the same manner, biometric comparison, e.g. for the purpose of performing face recognition of the subject, may be performed by a computer system external to the device. Under such circumstances, the device performs image capture and transmits data to the external computer system so that it performs identification or authentication.

Various face recognition methods may be implemented in the context of the invention. On this topic, reference may be made to the publication by Zhao et al., "Face recognition: a literature survey", ACM Computing Surveys, Vol. 35, No. 4, December 2003, pp. 399-458, which mentions various face recognition methods.

The device 1 shown in FIG. 1 further includes an iris image taking system 30 configured to take at least one image of one or both irises of the subject's eyes once the positions of the subject's eyes have been triangulated. In addition to the cameras 21, 22, and 23, the device 1 may thus include an iris image taking system 30 comprising an iris camera. The field $C_{30}$ of the iris image taking system 30 advantageously covers the entire acquisition volume V, as shown in FIG. 1. As shown, the iris image taking system 30 may be situated above the first and second cameras 21 and 22. The field angle $\beta_{30}$ in the vertical direction of the iris image taking system 30 may be different from, or in a variant it may be equal to, at least one of the field angles $\beta_{21}$, $\beta_{22}$ and $\beta_{23}$. In the example shown in FIG. 1, the field angle $\beta_{30}$ is about 60°.

The iris image taking system 30 is configured to be controlled at least by data associated with the positions of the subject's eyes as determined in the example shown in FIG. 1 by triangulation using the third camera 23 and at least one of the first and second cameras 21 and 22. The iris image taking system 30 may be electromechanical. As mentioned above, the iris image taking system 30 may be in communication with an iris recognition system configured to recognize at least one of the irises of the subject's eyes, the iris recognition system being incorporated in the device 1 or being situated outside it.

The example shown in FIG. 1 shows an iris image taking system 30 that is incorporated in the device 1, however it would not go beyond the ambit of the present invention for the iris image taking system to be outside the device. The device 1 shown in FIG. 1 also includes a man-machine interface screen 35 for attracting the gaze of the subject in order to optimize the face and iris recognition performance of the device 1. The screen 35 may also serve to display information, e.g. relating to the progress of the identification or authentication method, or to its results. As shown in FIG. 1, the screen 35 may be situated above the second camera 22 and below the third camera 23 when the device 1 is in an operating configuration.

The example shown makes use of three cameras to perform face recognition and triangulation, but it would not go beyond the ambit of the invention if a greater number of cameras were used. By way of example, it is possible for a device to have third and fourth cameras, each having a respective optical axis forming a non-zero angle relative to the optical axes of the first and second cameras, and intersecting those axes.

FIG. 2 shows a side view of the device 1 of the invention together with the acquisition volume V in which a subject S is positioned in order to be identified or authenticated. Possible values for the dimensions of the acquisition volume V are given below by way of example. Unless specified to the contrary, the heights relative to the acquisition volume, $h_{v,min}$, $h_{v,max}$, and $h_v$ as described below are measured perpendicularly to the positioning surface $S_p$.

The height $h_{v,min}$ of the bottom boundary 50 of the acquisition volume V may be greater than or equal to 80 cm, e.g. it may lie in the range 80 cm to 120 cm. By way of example, the height $h_{v,min}$ of the bottom boundary 50 of the acquisition volume is equal to 100 cm.

The height $h_{v,max}$ of the top boundary 51 of the acquisition volume V may be greater than or equal to 190 cm, e.g. it may lie in the range 190 cm to 210 cm. By way of example, the height $h_{v,max}$ of the top boundary 51 of the acquisition volume V is equal to 200 cm.

The height $h_v$ of the acquisition volume V, corresponding to $h_{v,max} - h_{v,min}$, may be greater than or equal to 70 cm, e.g. lying in the range 70 cm to 130 cm. By way of example, the height $h_v$ of the acquisition volume V is equal to 100 cm.

The depth $p_v$ of the acquisition volume V, measured along the normal axis Y, may be greater than or equal to 20 cm, for example it may lie in the range 20 cm to 80 cm. By way of example, the depth $p_v$ of the acquisition volume V may be equal to 40 cm.

The width $L_v$ of the acquisition volume V, measured perpendicularly to the normal axis Y and to the camera placement axis X, may be greater than or equal to 30 cm, for example it may lie in the range 30 cm to 80 cm. By way of example, the width $L_v$ may be equal to 50 cm.

The distance d between the third camera 23 and the acquisition volume V, as measured along the normal axis Y, may be greater than or equal to 30 cm, e.g. it may lie in the range 30 cm to 250 cm.

There follows a description of example methods of the invention for identifying or authenticating a subject.

In a first step a), the subject S takes up a position in the acquisition volume V. In order to help position the subject S, the position of the acquisition volume V may be identified by a visible indicator 40, e.g. formed on the positioning surface $S_p$ on which the subject S is to stand, as in the example shown in FIG. 2. It is possible to use other means for identifying the acquisition volume, such as physically defining all or part of the acquisition volume by means of one or more elements.

Once the subject S is positioned in the acquisition volume V, 2D face recognition processing is performed on the subject S using a device 1 as described above (step b)). 2D face recognition may be performed using images supplied by at least one of the first and second cameras 21 and 22. In a variant, or in combination, the 2D face recognition may be performed at least from images supplied by the third camera 23. This possibility may be advantageous for identifying or authenticating subjects who are relatively tall.

In order to perform 2D face recognition, data associated with the images supplied by the camera(s) used may be compared with reference data stored in a data storage medium.

Once the subject S is positioned in the acquisition volume V, a step c) is performed of determining the position of at least one zone of the subject's face, e.g. the eyes, by triangulation from the images supplied by at least two of the first, second, and third cameras. Step c) is initiated by a substep consisting in detecting the zone of the face in at least one 2D video stream supplied by at least one of the cameras. Thus, minimizing the angles between the optical axes of the cameras and the normal to the face of the subject for 2D face recognition is also advantageous for performing the triangulation step. As mentioned above, step c) may be performed before or after step b).

Once the position of the zone of the face of the subject S has been determined by triangulation, it is possible, e.g. by means of an electromechanical system, to guide the iris image taking system so as to recognize at least one of the irises of the subject's eyes with the help of an iris recognition system in communication with said iris image taking system.

On the basis of the position obtained for at least one zone of the face, it is possible to estimate a 3D model of the subject's face in order to perform 3D face recognition of the subject.

Iris or 3D face recognition may be performed by the device itself, or in a variant by a computer system external to the device.

The use of a common set of cameras, for performing both 2D face recognition and also 3D stereoscopy enables detection processing to be performed in common, thereby reducing requirements in terms of computation and thus advantageously reducing the cost of performing the method and reducing overall size, in particular because it is possible to reduce the number of cameras needed for similar performance.

Figure 3:
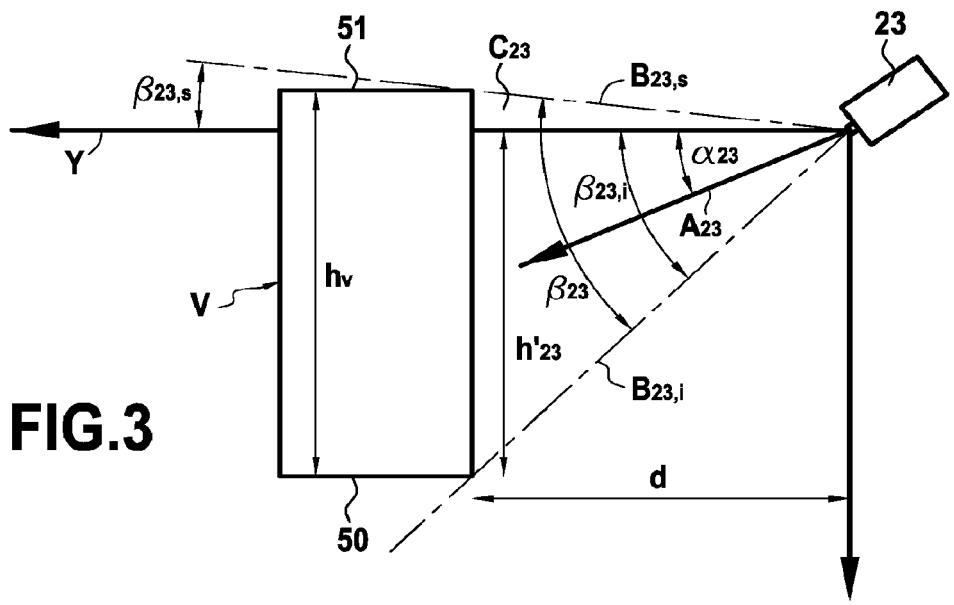
FIG. 3 is a highly diagrammatic and fragmentary view of a preferred angle of inclination for the optical axis of the third camera.

There follows a description of FIG. 3 and of determining the optimum value for the angle $\alpha_{23}$ between the optical axis $A_{23}$ of the first camera 23 and the normal axis Y.

In FIG. 3, the location is the same as above. The following terms are added:
- $h'_{23}$ designates the height of the third camera 23 measured relative to the height of the bottom boundary 50 of the acquisition volume V;
- the angle $\beta_{23,i}$ corresponds to the angle formed between the bottom edge $B_{23,i}$ of the field of the third camera 23 and the normal axis Y; and
- the angle $\beta_{23,s}$ corresponds to the angle formed between the top edge $B_{23,s}$ of the field of the third camera 23 and the normal axis Y.

There follows a description of the calculation for obtaining an analytic expression for the minimum angle of the optical axis of the third camera that makes it possible to cover the entire acquisition volume V in order to perform 3D triangulation throughout the volume with the help of the third camera. As explained above, having a minimum angle of inclination for the optical axis of the third camera advantageously serves to optimize the face recognition processing performed on the basis of the images supplied by the third camera.

The following apply:

$$\beta_{23,i} = \arctan(h'_{23}/d)$$

$$\alpha_{23} = \beta_{23,i} - \beta_{23}/2$$

This makes it possible to deduce the looked-for result:

$$\alpha_{23} = \arctan(h'_{23}/d) - \beta_{23}/2$$

There is an additional condition on the field angle $\beta_{23}$, since it is necessary to be able to perform triangulation throughout the acquisition volume V using the third camera, so the field angle $\beta_{23}$ must be large enough to ensure that the field $\beta_{23}$ of the camera 23 can cover the entire acquisition volume V. This leads to the following condition:

$$\beta_{23} \geq \arctan(h'_{23}/d) + \arctan((h_v - h'_{23})/d)$$

Figure 4:
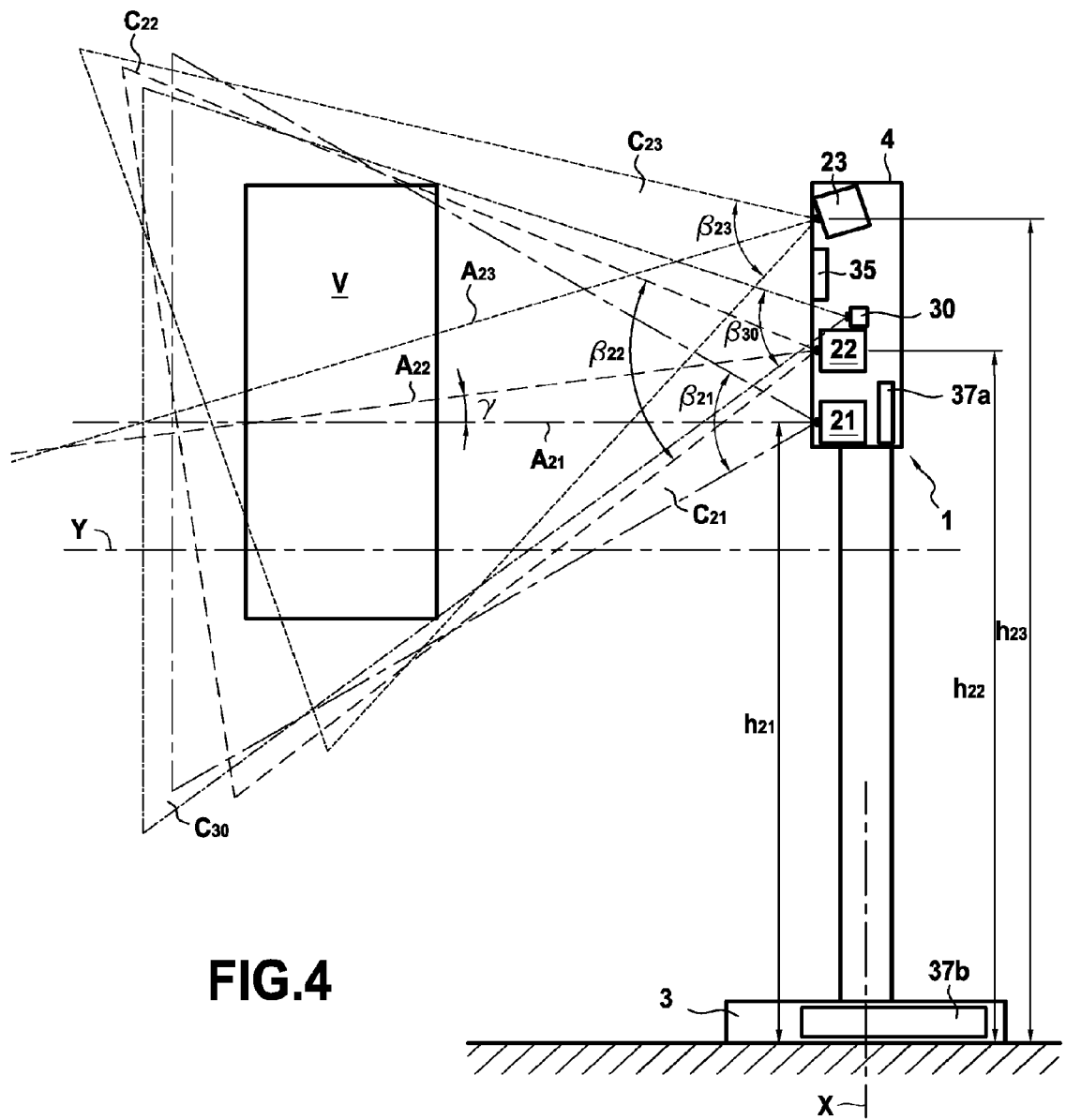
FIG. 4 is a fragmentary longitudinal section view of a variant device of the invention.

FIG. 4 shows a variant embodiment of the device of the invention. The only difference between the devices shown in FIGS. 1 and 4 is that, in FIG. 4, the optical axis $A_{22}$ of the second camera 22 slopes downwards a little (i.e. the optical axis $A_{22}$ of the second camera 22 extends towards the positioning surface on which the subject is to be present). The optical axis $A_{22}$ forms a non-zero angle $\gamma$ with the optical axis $A_{21}$ of the first camera 21. The angle $\gamma$ is less than 10°, e.g. less than or equal to 5°. The device 1 shown in FIG. 4 makes it possible to use triangulation to determine the position of at least one zone of the subject's face, e.g. the eyes, by using the first and second cameras 21 and 22. It is also possible to use the third camera 23 and at least one of the first and second cameras 21 and 22 in order to perform this triangulation in the device 1 shown in FIG. 4.

Naturally, it would not go beyond the ambit of the invention for the optical axis of the second camera to be parallel to the normal axis, and for the optical axis of the first camera to extend towards the positioning surface on which the subject is to be present. In a variant that is not shown, the optical axes of the first and second cameras both extend towards the positioning surface on which the subject is to be present.

Figure 5:
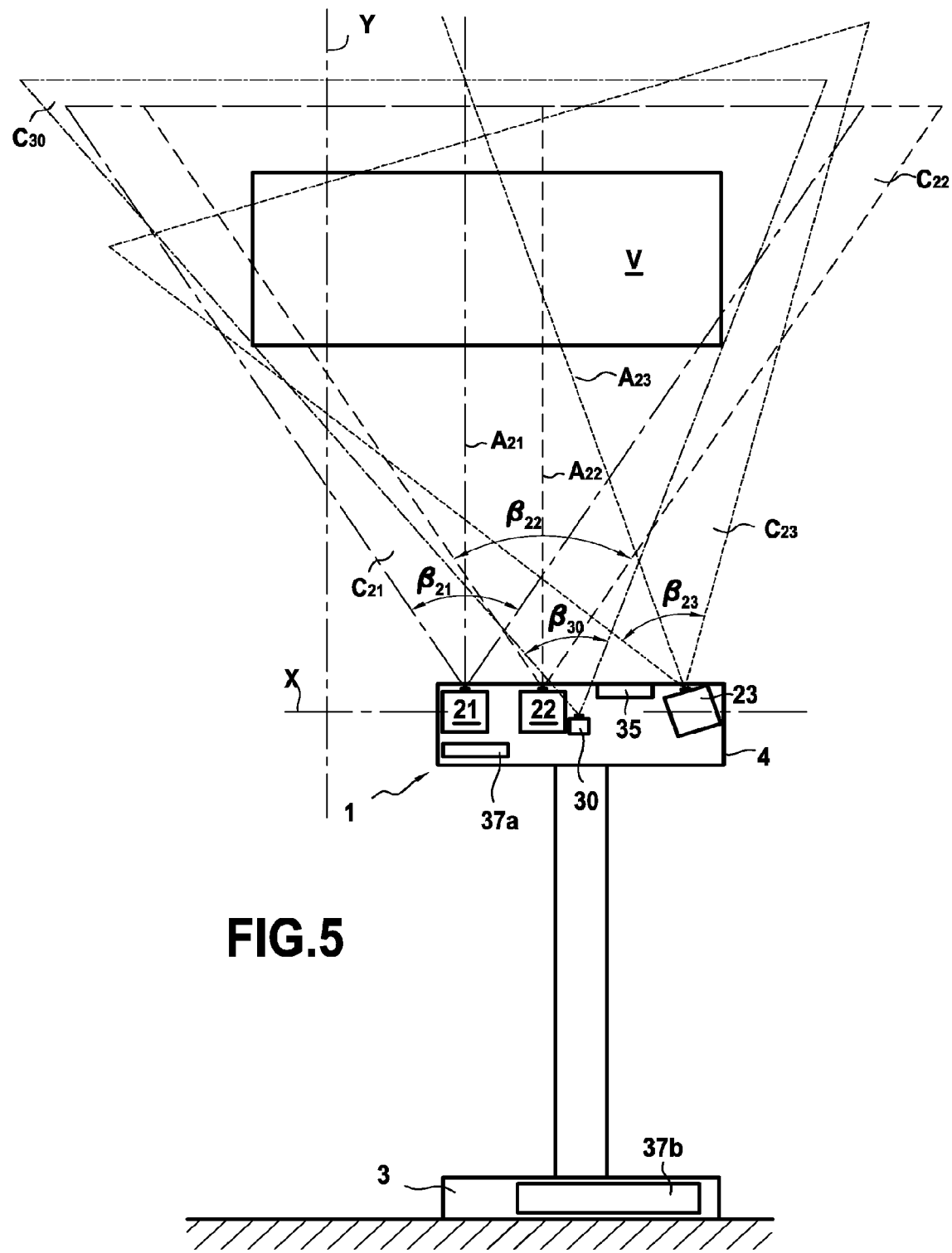
FIG. 5 is a fragmentary longitudinal section view of a variant device of the invention.

FIG. 5 shows a variant device of the invention. In this example, the camera placement axis X is parallel to the support surface $S_p$ on which the device 1 is placed, the device 1 thus "facing upwards". The first, second, and third cameras 21, 22, and 23 are successively offset along the axis X. Unlike the situation shown in FIG. 1, the placement axis X is now horizontal and the normal axis Y is vertical. During utilization of the device 1 as shown in FIG. 5, a user leans over the device 1 so as to place his or her face in the acquisition volume V in order to proceed with identification or authentication.

Figure 6A:
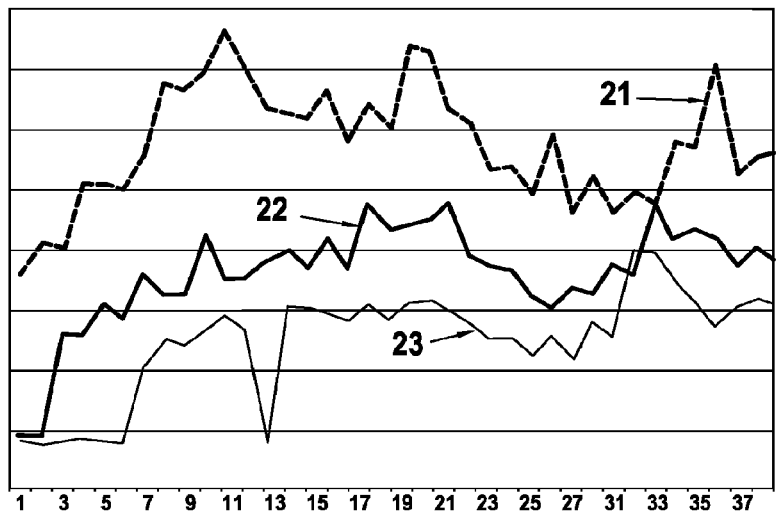
FIGS. 6A to 7B compare the performance of a device of the invention with the performance of a device not of the invention.
Figure 6B:
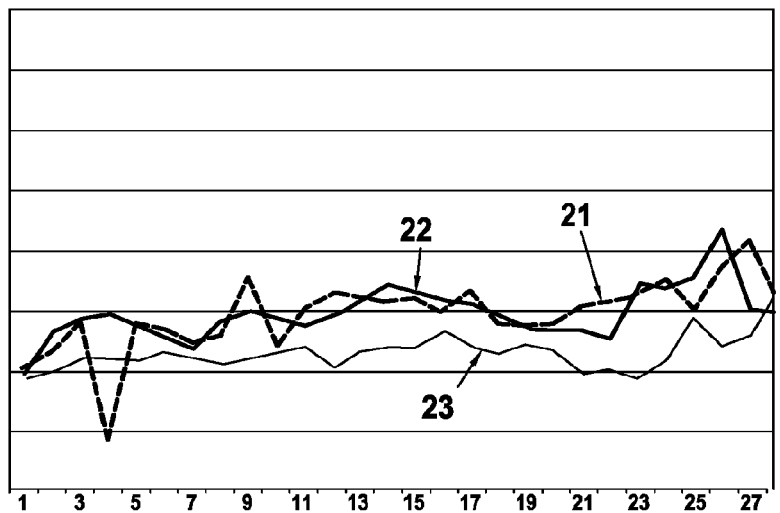

FIGS. 6A and 6B show comparative test results between a device of the invention (FIG. 6A) and a device outside the invention (FIG. 6B). The variable of the abscissa axis in the graphs of FIGS. 6A and 6B corresponds to the index of the image in a video sequence taken of a person of small size. The ordinate axis is similar between the two graphs and corresponds to a biometric comparison score. The only difference between the device outside the invention and the device of the invention used to perform the comparison tests lay in the angle made by the optical axis of the first camera and the normal axis. In the example device of the invention under test, the optical axes of the first and second cameras were both parallel to the normal axis and the optical axis of the third camera intersected them. In contrast, in the device outside the invention under test the optical axis of the first camera sloped upwards at an angle of 10° relative to the normal axis and the optical axis of the second camera was parallel to the normal axis (in the device outside the invention, the optical axes of the first and second cameras therefore did not form between them an angle strictly less than 10°). Thus, in the device of the invention under test, none of the optical axes of the cameras pointed upwards and the optical axes of the first and second cameras were horizontal.

The first camera of such a device of the invention performed much better recognition of subjects of small size compared with the device outside the invention (see the curve relative to the first camera, the bottom camera, curve 21). As mentioned above, such a result can be explained by the fact that in the configuration of the invention under test, the angle formed between the normal to the faces of subjects of small size and the optical axis of the first camera is minimized and by the fact that the optical axis of the first camera does not point upwards, thereby limiting as much as possible any dazzling of the first camera, e.g. by lighting situated high up.

Figure 7A:
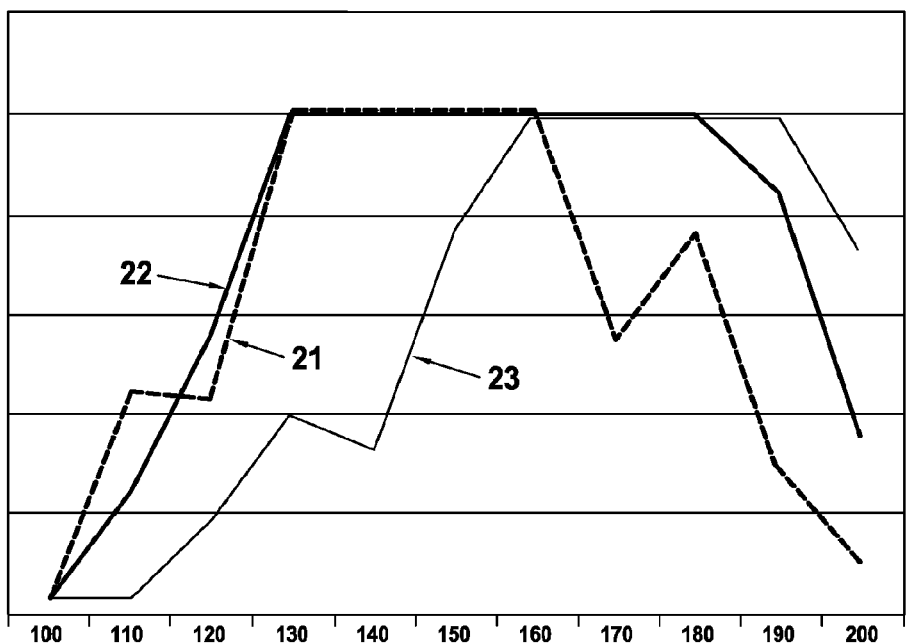
Figure 7B:
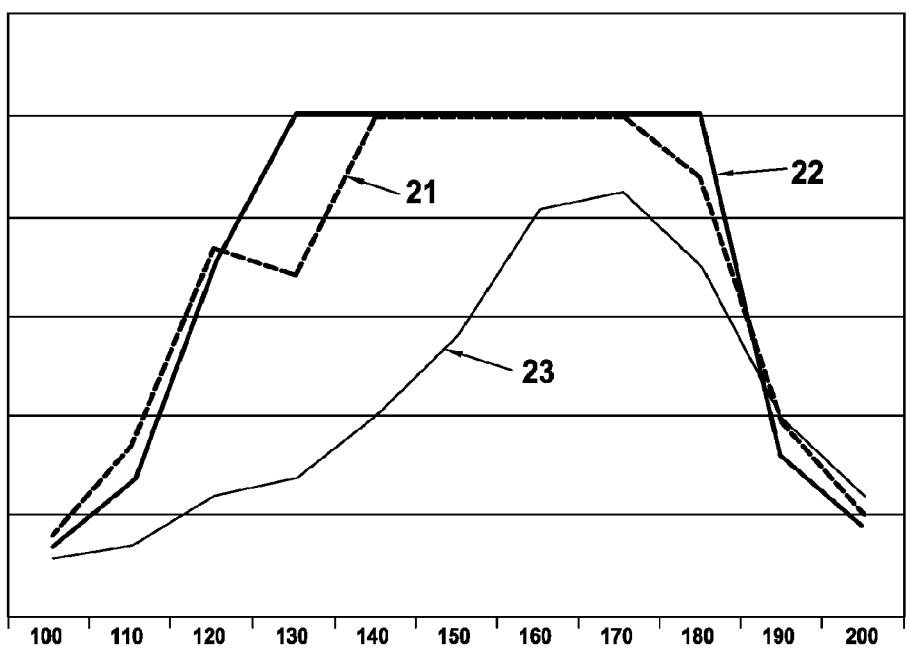

FIGS. 7A and 7B also show the results of comparative testing between a device of the invention and a device outside the invention. The abscissa axes in these figures represent the height in centimeters of the subject under evaluation. In the device of the invention under test (FIG. 7A), the optical axes of the first and second cameras were horizontal, whereas in the device outside the invention under test (FIG. 7B), the optical axis of the first camera sloped upwards at an angle of 10° relative to the normal axis, and the optical axis of the second camera was parallel to the normal axis. In addition to this difference, there was also a difference in the angles of inclination of the optical axes of third cameras in the devices under test. The angle of inclination of the optical axis of the third camera in the device outside the invention under test was greater than the angle of inclination of the optical axis of the third camera in the device of the invention under test so as to ensure that the optical axes of all three cameras coincided outside the acquisition volume in the device outside the invention under test.

In the device of the invention under test, the angle of inclination of the optical axis of the third camera corresponded to the minimum value for enabling 3D triangulation to be performed using the third camera throughout the acquisition volume V ($\alpha_{23}=\arctan(h'_{23}/d)-\beta_{23}/2$, as described with reference to FIG. 3).

A comparison between FIGS. 7A and 7B shows in particular that the device of the invention presented better performance for recognizing tall subjects because of the smaller angle between the normal to the faces of such subjects and the optical axis of the third camera (see the results obtained using the top camera, curve 23). It can also be seen that the device of the invention presented better performance for recognizing subjects of small size using the bottom camera 21 (see the results obtained with the bottom camera, curve 21).

The terms "including/containing/comprising a" should be understood as "including/containing/comprising at least one".

The term "lying in the range . . . to . . . " should be understood as including the end values.

The invention claimed is:

1. A device for use in identifying or authenticating a subject positioned in an acquisition volume on the basis of at least one biometric characteristic of the subject, the device comprising in succession, in offset manner along a camera placement axis:
    a first camera;
    a second camera; and
    a third camera, optical axes of the first and second cameras forming between them an angle strictly less than 10°, and an optical axis of the third camera intersecting the optical axes of the first and second cameras,
    the optical axes of the first and second cameras each forming an angle less than or equal to 5° relative to a normal axis perpendicular to the camera placement axis, and
    superposition of fields of the first and second cameras covering the entire acquisition volume, wherein the following conditions are satisfied:

angle $\alpha_{23}$ formed between the optical axis of the third camera and the normal axis perpendicular to the placement axis of the cameras is such that:

$(\arctan(h'_{23}/d)-\beta_{23}/2) \leq \alpha_{23} \leq 1.1 \times (\arctan(h'_{23}/d)-\beta_{23}/2)$, and a field angle $\beta_{23}$ along a height of the third camera satisfies the following condition:

$\beta_{23} \geq 2 \times (\alpha_{23}+\arctan((h_v-h'_{23})/d))$, where $h'_{23}$ designates the height of the third camera measured relative to a height of bottom boundary of the acquisition volume, $h_v$ designates a height of the acquisition volume, and d designates a distance measured along the normal axis between the third camera and the acquisition volume.

2. The device according to claim 1, wherein the optical axes of the first and second cameras are substantially parallel to each other.

3. The device according to claim 2, wherein the optical axes of the first and second cameras are both parallel to the normal axis.

4. The device according to claim 1, further comprising, in addition to the first, second, and third cameras, an incorporated iris image taking system in communication with an iris recognition system, said iris recognition system being configured to recognize at least one iris of the eyes of the subject from at least one image of one or both of the irises of the eyes of the subject as taken by the iris image taking system.

5. The device according to claim 4, wherein the iris image taking system is a system for taking an image of a portion of the texture of at least one iris.

6. The device according to claim 1, wherein:
    the first camera is placed at a first height $h_{21}$;
    the second camera is placed at a second height $h_{22}$ higher than the first height $h_{21}$; and
    the third camera is placed at a third height $h_{23}$ higher than the second height $h_{22}$.

7. The device according to claim 6, wherein the optical axis of the third camera extends towards a positioning surface on which the subject is to be present in order to perform identification or authentication, and the optical axes of the first and second cameras are both parallel to the normal axis.

8. The device according to claim 6, therein the optical axis of the third camera and at least one of the optical axes of the first and second cameras extend towards a positioning surface on which the subject is to be present in order to perform identification or authentication.

9. An automatic door fitted with the device according to claim 1.

* * * * *